(12) United States Patent
Wilson

(10) Patent No.: US 7,696,211 B2
(45) Date of Patent: Apr. 13, 2010

(54) METHODS AND PHARMACEUTICAL COMPOSITIONS FOR TREATING SEPSIS

(76) Inventor: Constance N. Wilson, P.O. Box 12076, 2 Davis Dr., Raleigh, NC (US) 27709-2076

( * ) Notice: Subject to any disclaimer, the term of this patent is extended or adjusted under 35 U.S.C. 154(b) by 0 days.

(21) Appl. No.: 11/412,754

(22) Filed: Apr. 27, 2006

(65) Prior Publication Data

US 2006/0276378 A1    Dec. 7, 2006

Related U.S. Application Data

(60) Provisional application No. 60/676,505, filed on Apr. 29, 2005.

(51) Int. Cl.
*A61K 31/52* (2006.01)
*A61K 31/43* (2006.01)
*A61K 31/545* (2006.01)
*A61K 31/515* (2006.01)
*A61K 31/505* (2006.01)

(52) U.S. Cl. .................... 514/263.1; 514/192; 514/200; 514/271; 514/272

(58) Field of Classification Search ............ 514/263.35, 514/271, 272, 263.1, 192, 200
See application file for complete search history.

(56) References Cited

U.S. PATENT DOCUMENTS

| | | | | |
|---|---|---|---|---|
| 5,089,274 | A * | 2/1992 | Marra et al. ................. | 424/534 |
| 5,730,980 | A * | 3/1998 | Ulevitch et al. ........... | 424/154.1 |
| 5,786,360 | A * | 7/1998 | Neely ..................... | 514/263.35 |
| 6,001,842 | A * | 12/1999 | Neely ........................ | 514/171 |

OTHER PUBLICATIONS

Young (Am J Med 1985, Aug 9, 79 (2A), 89-95).*
Motew et al. (Shock, vol. 7, 6, 439-446, 1997).*
Neely et al. (The Am. Physiological Society, 1997, p. 1353-1361).*
Bochud et al. (Intensive Care Med, 2001, 27, S33-S48).*
Bartlett Sepsis document (p. 1-9), 2009.*
Nadeem, A., and S. J. Mustafa, "Adenosine Receptor Antagonists and Asthma," *Drug Discovery Today: Therapeutic Strategeis/Respiratory Diseases*, 2006, pp. 269-275, vol. 3(3).
Nadeem, A., et al., "Adenosine $A_1$ Receptor Antagonist Versus Montelukast on Airway Reactivity and Inflammation," *European Journal of Pharmacology*, 2006, pp. 116-124, vol. 551.
Obiefuna, P.C.M., "A Novel $A_1$ Adenosine Receptor Antagonist, L-97-1 [3-[2-(4-Aminophenyl)-ethyl]-8-benzyl-7-{2-ethyl-(2hydroxy-ethyl)-amino]-ethyl}-1-propyl-3,7-dihydro-purine-2,6-dione], Reduces Allergic Responses to House Dust Mite in an Allergic Rabbit Model of Asthma," *The Journal of Pharmacology and Experimental Therapeutics*, 2005, pp. 329-336, vol. 315(1), (Oct.)
George Gallos, Thomas D. Ruyle, Charles W. Emala and H. Thomas Lee; A1 Adenosine Receptor Knockout Mice Exhibit Increased Mortality, Renal Dysfunction, and Hepatic Injury in Murine Septic Peritonitis; AJP—Renal Physiology, Mar. 22, 2005, Bethesda MD USA.

* cited by examiner

*Primary Examiner*—Sreeni Padmanabhan
*Assistant Examiner*—Umamaheswari Ramachandran
(74) *Attorney, Agent, or Firm*—Jim Passé; Passe Intellectual Property, LLC

(57) ABSTRACT

Methods and compositions for treating and preventing sepsis are provided. The methods of the invention comprise administering to a subject a therapeutically effective amount of an A1 adenosine receptor antagonist in combination with an antibiotic agent. The invention further encompasses pharmaceutical compositions comprising a combination of an A1 adenosine receptor antagonist and an antibiotic agent in a pharmaceutically acceptable carrier. The pharmaceutical compositions of the invention find use in methods for treating and preventing sepsis.

7 Claims, 4 Drawing Sheets

Figure 1. L-97-1 (mg/kg/hr) was administered as a single 8 hour infusion post-CLP.

METHODS AND PHARMACEUTICAL COMPOSITIONS FOR TREATING SEPSIS

CROSS REFERENCE TO RELATED APPLICATIONS

This application claims the benefit of U.S. Provisional Application Ser. No. 60/676,505, filed Apr. 29, 2005, which is incorporated herein by reference in its entirety.

FEDERALLY SPONSORED RESEARCH OR DEVELOPMENT

This invention was made with United States Government support under grant number 1 R41 AI056603-01A1 awarded by the National Institutes of Health. The government has certain rights in the invention.

FIELD OF THE INVENTION

The present invention relates to methods and compositions for the treatment of sepsis.

BACKGROUND OF THE INVENTION

Sepsis is a medical syndrome characterized by an overwhelming systemic response to infection that can rapidly lead to shock, organ failure and death. Sepsis may also lead to the development of adult respiratory distress syndrome (ARDS), a life-threatening condition in which inflammation of the lungs and accumulation of fluid in the air sacs (alveoli) leads to low blood oxygen levels. According to data presented at the 67th annual scientific meeting of the American College of Chest Physicians in Philadelphia, the incidence of sepsis in the United States increased by 23.3% from 1988 to 1998. In the U.S., sepsis is the 10th leading cause of death overall, accounting for over 750,000 cases and 215,000 deaths each year and $17 billion in annual health care expenditures. Moreover, the incidence of sepsis may be rising due to the increasing age of the population, growing numbers of immunocompromised patients, use of life-sustaining technologies, and increased resistance of bacteria to antimicrobial agents.

Sepsis may be caused by bacterial (either Gram-positive or Gram-negative), fungal, viral, and other infections. Although sepsis can follow any bacterial infection, it is often associated with a Gram-negative bacterial infection. It is generally accepted that approximately 50% of sepsis cases due to bacterial infections are caused by Gram-negative bacteria. Most of the damage associated with Gram-negative sepsis comes not from the invasion of bacteria per se but from the endotoxin present in the cell wall of the bacteria. Endotoxin or lipopolysaccharide (LPS) is a toxin released from Gram-negative bacteria. Following its release into the blood stream from a site of infection, such as the lung, abdomen, or urinary tract, endotoxin acts on a number of different cell types, and induces a complex cascade of cellular, mediator and cytokine-related events. This inflammatory cascade results in organ (e.g., lung and kidney) damage, shock and death in patients with Gram-negative septicemia (endotoxemia). Based on the current understanding of how endotoxin induces this complex cascade of events, specific therapies developed in the past or currently in development attempt to target specific events in this cascade.

Endotoxin is released during growth, death and lysis of Gram-negative bacteria. See, for example, Rietschel et al. (1994) *FASEB J* 8:217-225; Hurley (1995) *Clin. Microbiol. Rev.* 8:268-292; and Mayeux (1997) *J Tox. Environ. Health* 51:415-435. Following its release into the circulation, endotoxin activates complement, coagulation, and kinin cascades. Endotoxin binds with an acute phase serum protein, LPS binding protein (LBP), and soluble CD14 (sCD14) to form LPS-LBP and LPS-sCD14 complexes. See Mayeux (1997) *J Tox. Environ. Health* 51:415-435; Chen et al. (1992) *Curr. Topics Microbiol. and Immunol.* 181:169-188; and Pugin et al. (1993) *Proc. Natl. Acad. Sci.* 90:2744-2748. These complexes then bind to specific binding proteins or specific cell membrane receptors on a number of different cell types, including vascular endothelial cells, neutrophils, and macrophages to induce the release of oxygen free radicals, nitric oxide, metabolites of arachidonic acid, including thromboxane (TXA2), prostacyclin, and platelet activating factor (PAF), and cytokines including tumor necrosis factor-$\alpha$ (TNF-$\alpha$), interleukin-1 (IL-1), and IL-6. See Mayeux (1997) *J Tox. Environ. Health* 51:415-435; Chen et al. (1992) *Curr. Topics Microbiol. and Immunol.* 181:169-188; Pugin et al. (1993) Proc. Natl. Acad. Sci. 90:2744-2748; Akarasereenont et al. (1995) *Eur. J Pharmacol.* 273: 121-128; Brigham and Meyrick (1986) Am. Rev. Respir. Dis. 133:913-927; Morrison (1987) *Ann. Rev. Med.* 38:417-432; and Schletter et al. (1995) *Arch. Microbiol.* 164:383-389. These mediators and cytokines exert direct cytotoxic effects, promote neutrophil activation and migration, promote upregulation of adhesion molecules for neutrophils on endothelial cells, prime macrophages to the effects of endotoxin-induced cytokine release, and produce cardiovascular effects, including myocardial depression, vascular relaxation, and pulmonary hypertension that are important in the pathophysiology of endotoxin-induced organ injury and cardiovascular collapse. See generally See Mayeux (1997) *J Tox. Environ. Health* 51:415-435; Chen et al. (1992) *Curr. Topics Microbiol. and Immunol.* 181:169-188; Pugin et al. (1993) *Proc. Natl. Acad. Sci.* 90:2744-2748; Akarasereenont et al. (1995) *Eur. J Pharmacol.* 273: 121-128; Brigham and Meyrick (1986) *Am. Rev. Respir. Dis.* 133:913-927; Morrison (1987) *Ann. Rev. Med.* 38:417-432; Schletter et al. (1995) *Arch. Microbiol.* 164:383-389; Hoshino et al. (1999) *J Immunol.* 162: 3749-3752; Poltorak et al. (1998) *Science* 282: 2085-2088; and Martin and Silverman (1992) *Clin. Infect. Dis.* 14:1213-1228.

Endotoxin levels are increased in patients at risk of adult respiratory distress syndrome (ARDS), in patients with Gram-negative septicemia and ARDS, and in patients with septic shock and multisystem organ failure. See Parsons et al. (1989) *Am. Rev. Respir. Dis.* 140:294-301; Brandtzaeg et al. (1989) *J Infect. Dis.* 159:195-204; and Danner et al. (1991) *Chest* 99:169-175. There is a growing body of scientific information supporting the concept that endotoxin initiates this complex "sepsis cascade" of events that results in organ damage and septic shock by binding to a receptor on endothelial cells to induce the release of cytotoxic substances which produce early endothelial cell damage. In the lung, endotoxin causes structural changes in the microvasculature, resulting in disruption of the blood-air barrier, interstitial and alveolar edema, neutrophil and macrophage cellular infiltration, and hemorrhage. These effects of endotoxin in the lung are dose-dependent. See, for example, Neely et al. (1997) *Am J Physiol. Lung* 272:L353-L361 and Meyrick et al. (1986) *Am. J Pathol.* 122:140-151. The direct effect of endotoxin on pulmonary arterial endothelial cells (PAECs), include contracture and widening of interendothelial junctions, cytotoxic effects such as "ruffling" of the surface, prominent cytoplasmic extensions, and nuclear crenation. Meyrick, supra. These electron micrographic changes in PAECs occur as early as 30 minutes following exposure to endotoxin and are associated with changes in permeability. Id. This direct cytotoxic effect of endotoxin on PAECs is dependent on the dose of endotoxin and the presence of serum and is independent of the presence of neutrophils and macrophages. See, for example, Meyrick, supra; Brigham et al. (1987) *J Appl. Physiol.* 63(2):840-850; Maeda et al. (1995) *Shock* 3:46-50; and Meyrick et al. (1989) *J Cellular Physiol.* 138:165-174. In addition, endotoxin-induced cytotoxicity of PAECs is associated with the release of oxygen free radicals and by products of lipid peroxidation, e.g. TXA2. See Brigham, supra and Conary et al. (1994) *J Clin. Invest.* 93:1834-1840.

Previously, it was reported that A1 adenosine receptor (AR) antagonists block endotoxin-induced acute lung injury (ALI) in animals. See Neely et al. (1997) *Am J Physiol. Lung* 272:L353-L361. In spontaneously breathing, intact-chest cats, in an isolated perfused left lower lobe of the lung, under conditions of controlled blood flow and constant left atrial pressure, endotoxin [15 mg/kg, intralobar arterial (i.a) infusion] produced ALI. Endotoxin (15 mg/kg, i.a.)-induced alveolar injury was blocked in a highly significant manner by A1 adenosine receptor antagonists, 1,3-dipropyl-8-cyclopentylxanthine (DPCPX) and bamiphylline. Furthermore, it has also been reported that endotoxin binds to and activates A1 adenosine receptors on human PAECs to induce the release of TXA2 and IL-6. Wilson et al. (2002) *J Endotoxin Res.* 8:263-271. Both TXA2 and IL-6 are cytotoxic to endothelial cells. See Zamora et al. (1993) *J Appl Physiol* 74:224-229 and Gornikiewicz et al. (2000) *FASEB J* 14:1093-1100. These data suggest that by activating A1 adenosine receptors on PAECs, endotoxin produces cytotoxicity of PAECs that ultimately leads to disruption of the blood-air barrier, interstitial and alveolar edema, neutrophil and macrophage cellular infiltration, as well as hemorrhage in endotoxin-induced ALI. Thus, A1 adenosine receptor antagonists may be useful in minimizing or preventing endotoxin-induced organ (e.g., lung) damage associated with sepsis.

Today, therapy for sepsis includes antibiotics, surgical drainage of the site of suspected infection, inotropes and vasopressors to support the heart and blood pressure, and supportive care in an intensive care unit, including mechanical ventilation. Despite the availability of newer antimicrobial agents and improved supportive care, the mortality for severe sepsis and septic shock of 30-60% remains high, and the outcome remains poor for patients with septicemia. These discouraging statistics suggest a need for additional therapies (adjuvant therapies) to this conventional approach to sepsis, which interrupt the complex cascade of events leading to shock, multi-system organ dysfunction, and death. Adjuvant anti-sepsis therapies would ideally prevent organ damage, shock, and death and improve outcome without interfering with the normal host innate immune response to bacterial infection.

A number of pharmaceutical companies have tried and failed to develop adjuvant anti-sepsis therapies. These companies have tried to develop drugs with anti-endotoxin, anti-cytokine, and other therapeutic properties for the treatment of sepsis. These attempts have failed to demonstrate a beneficial effect in patient outcome. Therefore, a need exists for more effective methods and compositions for treating sepsis.

BRIEF SUMMARY OF THE INVENTION

Methods and compositions for treating sepsis are provided. The methods of the invention comprise administering to a subject a therapeutically effective amount of an A1 adenosine receptor antagonist in combination with an antibiotic agent. The combination of an A1 adenosine receptor antagonist and an antibiotic agent promotes a desired therapeutic response. The A1 adenosine receptor antagonist and antibiotic agent may be administered simultaneously or sequentially and as a single pharmaceutical composition or as separate pharmaceutical compositions, each comprising an A1 adenosine receptor antagonist or an antibiotic agent. Methods of the invention find use in treating subjects currently suffering from sepsis and patients at risk for developing sepsis.

A pharmaceutical composition comprising an A1 adenosine receptor antagonist of the invention and an antibiotic agent in a pharmaceutically acceptable carrier is also provided. The pharmaceutical compositions of the invention find use in methods for treating sepsis.

DETAILED DESCRIPTION OF THE INVENTION

Figure 1:
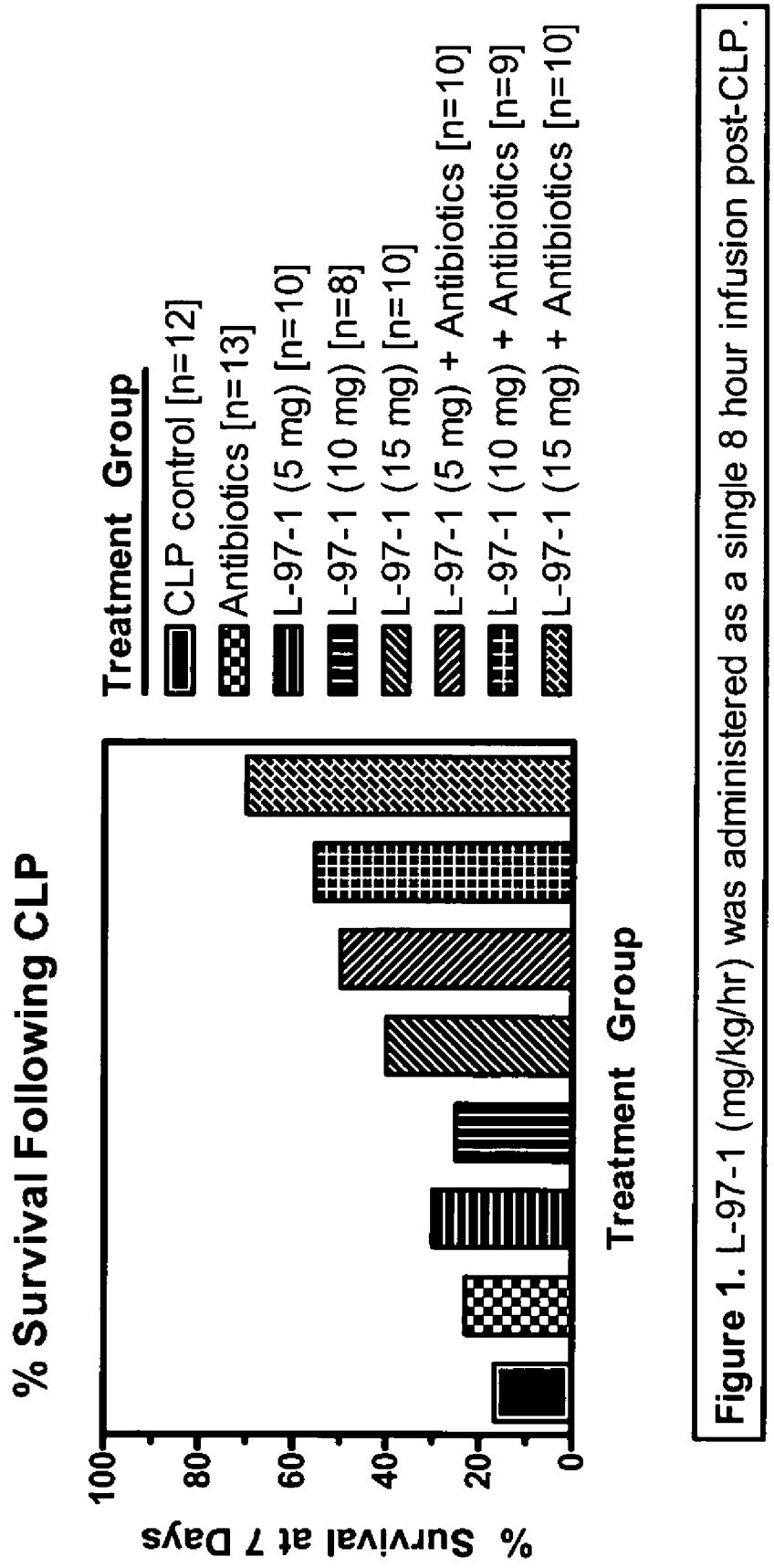
FIG. 1 summarizes the seven day survival rates for rats post-CLP treated with vehicle, antibiotics alone, L-97-1 alone, or L-97-1 and antibiotics. Experimental details are provided in Example 3.

The present invention is directed to methods and compositions for treating sepsis. The methods comprise administering to a subject a therapeutically effective amount of an A1 adenosine receptor antagonist in combination with an antibiotic agent. A1 adenosine receptor antagonists are known in the art and include, for example, those compounds described in U.S. Pat. Nos. 5,786,360 and 6,489,332 and in co-pending U.S. application Ser. Nos. 10/780,296, entitled "A1 Adenosine Receptor Antagonists," filed Feb. 17, 2004, Ser. No. 10/861,677, entitled "A1 Adenosine Receptor Antagonists," filed Jun. 4, 2004, and Ser. No. 10/560,853, entitled "A1 Adenosine Receptor Antagonists," filed Jun. 7, 2004, all of which are herein incorporated by reference in their entirety. In some embodiments, the A1 adenosine receptor antagonist comprises a compound of formula (I):

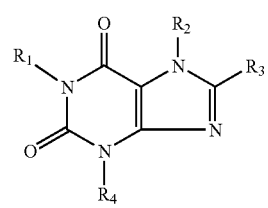

wherein $R_1$ is selected from the group consisting of $C_1$-$C_8$ alkyl;

$R_2$ is of the formula:

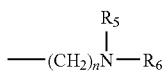

wherein n is an integer ranging from 1 to 8; $R_5$ is H or $CH_3(CH_2)_p$, wherein p is an integer ranging from 1 to 7; and $R_6$ is H; $(CH_2)_mH$; or $(CH_2)_mOH$, wherein m is an integer ranging from 1 to 8;

$R_3$ is:

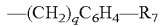

wherein q is an integer ranging from 1 to 8; wherein $R_7$ is selected from the group consisting of H, OH, $NH_2$, $R_9COOH$, wherein $R_9$ is an alkylene or alkenylene group having 1 to 8 carbon atoms, and $(CH_2)_tOH$, wherein t is an integer ranging from 1 to 8; and $R_4$ is of the formula:

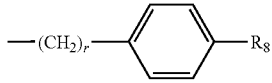

wherein $R_8$ is selected from the group consisting of H, $NH_2$, OH, $(CH_2)_fNH_2$ wherein f is an integer ranging from 1 to 8, $(CH_2)_sOH$, wherein s is an integer ranging from 1 to 8, and $R_{10}COOH$, wherein $R_{10}$ is an alkylene or alkenylene group having 1 to 8 carbon atoms; and r is an integer ranging from 1 to 8. Methods for synthesizing the A1 adenosine receptor antagonists of the invention are known in the art and are described in, for example, U.S. Pat. Nos. 5,719,279, 5,786,360, and 6,489,332. Variations of the foregoing will be obvious to those skilled in the art of synthetic organic chemistry.

In a particular aspect of the invention, the A1 adenosine receptor antagonist is designated L-97-1 and comprises the compound of formula (I), wherein:

$R_1$ is $C_3$ alkyl;

$R_2$ is:

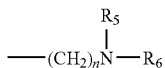

wherein n is 2; $R_5$ is $CH_3(CH_2)_p$, wherein p is 1; and $R_6$ is $(CH_2)_mOH$, wherein m is 2;

$R_3$ is:

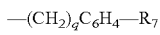

wherein q is 1; wherein $R_7$ is H; and $R_4$ is of the formula:

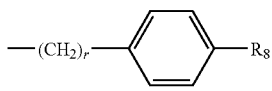

wherein $R_8$ is $NH_2$; and r is 2.

Pharmaceutical compositions comprising an A1 adenosine receptor antagonist of the invention and an antibiotic agent are also provided. Methods of using these pharmaceutical compositions in the treatment and prevention of sepsis are further disclosed.

By "antibiotic agent" is intended any substance which inhibits the growth of or kills susceptible bacteria or other microorganisms. Any antibiotic agent or combination of antibiotic agents may be used to practice the invention. Antibiotic agents include but are not limited to β-lactams (e.g., penicillin, ampicillin, cefuroxime, ceftazidime, and imipenem), aminoglycosides (e.g., gentamicin, amikacin, kanamycin, tobramycin, and netilmicin), carbapenems, cephalosporins (e.g., cefotaxime, moxalactam, and cefoperazone), penicillin, amoxicillin, clindamycin, carboxypenicillins (e.g. ticarcillin), ureidopenicillins (e.g., piperacillin), β-lactamase inhibitors (e.g., clavulanic acid and tazobactam), fluoroquinones (e.g., ciprofloxacin, norfloxacin, and levofloxacin), glycopeptides (e.g., vancomycin and teicoplanin), oxazolidinones (e.g., linezolid), streptogramins (e.g., quinupristin/dalfopristin), monobactams (e.g., aztreonam), and polymyxins (e.g., polymyxin B and polymyxin E (i.e., colistin)). See generally Bochud et al. (2004) *Crit. Care Med* 32(11) 495-512 and Harris and Thorarensen (2004) *Curr. Med. Chem.* 11:2213-2243, both of which are herein incorporated by reference in their entirety. Furthermore, antibiotic agents may include sulfonamides, chloramphenicol, tetracyclines, macrolides, lincosamides, rifamycins, nitromidiazoles, quinolones, trimethoprim, and lipopeptides. Powers (2004) *Clin. Microbiol. Infect.* 10 (Supp. 4):23-31 (See particularly p. 24, Table 1).

Antibiotic agents may include those from new emerging classes of antibiotics including, inhibitors of DNA methyltransferase, pyrrole tetramide DNA binders, heteroaromatic polycyclic (HARP) compounds, anti-bacterial DNA binders, benzamides, benzothiophenes, isoquinoline analogs, gyrase inhibitors, pyrido [1,2-c] pyrimidine gyrase inhibitors, benzimidazole/benzoxazole gyrase inhibitors, quinazolinedione gyrase inhibitors, PcrA inhibitors, inhibitors of RNA polymerase, RNA bacterial ribosome targets, including protein synthesis inhibitors, inhibitors of RNA-protein interactions (complexes), transcriptional/translational inhibitors, paromomycin, elongation inhibitors, translation inhibitor TAN-1057, aminoacyl-tRNA synthetase inhibitors, chuangximycin analogs, peptide deformylase (PDF) inhibitors, bacterial cell wall inhibitors, including UDP-N-aceytylmuramate/L-alanine ligase (Mur C) and other mur (D and I) inhibitors, as well as phosphor-N-acetylmuramyl-pentapeptide translocase (Mra Y), including muraymycin C1, muraymycin A1, mureidomycin A, liposidomycin C, RU75411, penicillin binding protein (PBP) inhibitors, inhibitors of bacterial cell membranes, including inhibitors of lipid A biosynthesis, metalloenzyme inhibitors, hydroxamic acid inhibitors, including BB-78484, BB-78485, inhibitors of 3-deoxy-D-manno-2-octulosonate-8-phosphate synthetase (KDOP), mutulin derivatives, althiomycin and analogs of althiomycin, naphthyridine agents, pyrimidine-pyridine analogs, piperidine agents, tetrahydroquinoline analogs, mannopeptimycin, AC-98-5, AC-98-6446, phosphoryl transfer system (PTS) inhibitors, AI-2 signaling pathway inhibitors, dehydroquinate synthetase (DHQS) inhibitors, Ar-358, shikimate kinase inhibitors, chorismate synthase (CS) inhibitors, PTX110130, PTX008313, nicotinamide adenine dinucleotide (NAD) synthetase inhibitors, fatty acid biosythesis inhibitors, thiolactomycin, triclosan, isoniazid, cerulenin, phosphopantetheine adenylyltransferase (PPAT) inhibitors, PTX-042695, PTX-031553, PTX-007063, PTX-008134, Fab inhibitors, β-ketoacyl-acyl carrier protein (ACP) synthase III (FABH) inhibitors, thiolactomycin analogs, enoyl-ACP reductase (FabI or FabK) inhibitors, SB-627696, SB-663042, and SB-633857. See generally Harris and Thorarensen, supra.

In a particular embodiment of the invention, the antibiotic agent is a broad-spectrum antibiotic. Antibiotic agents of particular interest include but are not limited to gentamicin, tobramycin, clinamycin, cefotaxime, amikacin, imipenem, netilycin, ceftazidime, cefuroxamine, metronidazole, cefazolin, cefoperazone, ceftriaxone, mezlocilin, ampicillin, amoxiclav, piperacillin, tazobactam, and ciprofloxacin. See, for example, Bochud et al., supra (particularly Tables 1 and 2). One of skill in the art will appreciate that the choice of antibiotic agent will be influenced by the susceptibility patterns of microorganisms in the community and in the particular hospital. While the methods of the invention require the administration of at least one antibiotic agent in combination with an A1 adenosine receptor antagonist, the use of multiple antibiotics (e.g., 2, 3, 4, 5, or more antibiotics) is also encompassed herein.

The methods and compositions of the invention are useful in treating sepsis. Sepsis is a systemic inflammatory response to infection. Sepsis refers to a syndrome describing a heterogenous constellation of symptoms. The "gold standard" laboratory test used to diagnose sepsis is a blood culture that is positive for pathogenic bacteria. Frequently, however, blood cultures from septic patients are not positive, and other laboratory tests lack specificity for diagnosing sepsis. Therefore, providing an adequate definition of sepsis has proved difficult for clinicians. Dremsizov et al. (2004) *Intl. J. Artificial Organs* 27(5):352-359, which is herein incorporated by reference in its entirety. At a recent conference of the American College of Chest Physicians (ACCP) and the Society of Critical Care Medicine (SCCM), a set of definitions for the terms sepsis, severe sepsis, and septic shock was developed. Levy et al. (2003) *Crit. Care Med.* 31(4):1250-1256, herein incorporated by reference. "Sepsis" was defined by the presence of both infection and a systemic inflammatory response. Infection was defined by the Conference as a pathologic process caused by the invasion of normally sterile tissue, fluid, or a body cavity by pathogenic or potentially pathogenic microorganisms. Id. Possible signs of systemic inflammation in response to infection include but are not limited to fever, hypothermia, tachycardia, tachypnea, altered mental status, significant edema or positive fluid balance, hyperglycemia, leukocytosis, leukopenia, normal WBC with greater than 10% immature forms, abnormally high plasma C-reactive protein, abnormally high plasma procalcitonin levels, arterial hypotension, arterial hypoxemia, acute oliguria, increased creatinine, coagulation abnormalities, ileus (absent bowel sounds), thrombocytopenia, hyperbilirubinemia, hyperlactatemia, and decreased capillary refill or mottling. Id. Within hours or days, sepsis may progress to spontaneous clotting in the blood vessels, severe hypotension, acute organ damage (e.g., acute lung injury (ALI)), multiple organ system failure, and death. The conference defined severe sepsis as sepsis with the further complication of organ dysfunction. Scoring systems for assessing and monitoring organ dysfunction are known in the art. See, for example, Bota et al. (2002) *Intens. Care Med.* 28:1619-1624 and Ferreira et al. (2005) *J Amer. Med. Assoc.* 286(14):1754-1758. Septic shock was defined as severe sepsis accompanied by acute circulatory failure characterized by persistent arterial hypotension unexplained by other causes. Arterial hypotension refers to a systolic arterial pressure below 90 mm Hg for adults. Methods and laboratory tests for assessing the clinical symptoms (and the improvement or worsening thereof) of sepsis, severe sepsis, and septic shock are well known in the art.

The term "sepsis" as used herein is inclusive of sepsis, septicemia (bacteremia/endotoxemia), severe sepsis, septic shock, and related conditions, as well as the clinical symptoms and complications associated with each of these conditions. The methods of the invention find use, for example, in ameliorating the inflammatory symptoms of sepsis described herein above, preventing, limiting, or treating ventilator-acquired pneumonia, preventing or limiting tissue or organ damage (e.g., endotoxin-induced lung damage), shock, and death, and generally improving the outcome of septic patients.

The methods of treatment of the present invention are not intended to be limited to particular subjects. A variety of subjects, particularly mammals, are contemplated. Subjects of interest include but are not limited to humans, dogs, cats, horses, pigs, cows, and rodents. In particular embodiments, the subject is a human. The subjects of the invention may be suffering from the symptoms of sepsis or may be at risk for sepsis (e.g., surgical patients, immunocompromised patients, etc.).

"Treatment" is herein defined as the administration of an A1 adenosine receptor antagonist in combination with the administration of an antibiotic agent to a subject, where the subject has sepsis or a symptom of sepsis, where the purpose is to cure, heal, alleviate, relieve, alter, remedy, ameliorate, improve, or affect the condition or the symptoms of sepsis. By "treatment" is also intended that the combination of the Al adenosine receptor antagonist and the antibiotic agent is administered to the subject as part of a single pharmaceutical composition, or alternatively as part of individual pharmaceutical compositions, each comprising either the A1 adenosine receptor antagonist or the antibiotic agent, where the subject has sepsis or a symptom of sepsis, where the purpose is to cure, heal, alleviate, relieve, alter, remedy, ameliorate, improve, or affect the condition or at least one of the symptoms of sepsis. Methods for preventing sepsis are also provided. By "preventing sepsis" is intended that an A1 adenosine receptor antagonist in combination with an antibiotic agent are administered to a subject at risk for sepsis in order to prevent the development of sepsis.

The methods of the invention comprise using a combination therapy. The term "combination" is used in its broadest sense and means that a subject is treated with at least two therapeutic agents, more particularly an A1 adenosine receptor antagonist and an antibiotic agent. The timing of administration of the A1 adenosine receptor antagonist and the antibiotic agent can be varied so long as the beneficial effects of the combination of these agents are achieved. The phrase "in combination with" refers to the administration of an A1 adenosine receptor antagonist with an antibiotic agent either simultaneously, sequentially, or a combination thereof. Therefore, a subject undergoing a combination therapy of the invention can receive the A1 adenosine receptor antagonist and the antibiotic agent at the same time (i.e., simultaneously) or at different times (i.e., sequentially, in either order, on the same day or on different days), so long as the therapeutic effect of the combination of both agents is achieved in the subject undergoing therapy. Where the A1 adenosine receptor antagonist and the antibiotic agent are administered simultaneously, they can be administered as separate pharmaceutical compositions, each comprising either an A1 adenosine receptor antagonist or an antibiotic agent, or can be administered as a single pharmaceutical composition comprising both agents.

The methods of the invention comprise administering to a subject a therapeutically effective amount of an A1 adenosine receptor antagonist in combination with an antibiotic agent. Any method for administering a composition to a subject may be used in the practice of the invention. Examples of possible routes of administration include parenteral, (e.g., intravenous (IV), intramuscular (IM), intradermal, subcutaneous (SC), or infusion), oral, pulmonary (e.g., inhalation), nasal, transdermal (topical), transmucosal, and rectal administration. By "therapeutically effective dose," "therapeutically effective amount," or "effective amount" is intended an amount of the A1 adenosine receptor antagonist that, when administered in combination with an amount of an antibiotic agent, brings about a positive therapeutic response with respect to treatment of a subject for sepsis. In particular embodiments, a therapeutically effective dose of the A1 adenosine receptor antagonist for oral administration is in the range from about 0.1 mg/kg to about 50 mg/kg. In other embodiments, a therapeutically effective dose of the A1 adenosine receptor antagonist for intravenous administration is in the range from about 0.001 mg/kg to about 25 mg/kg.

"Positive therapeutic response" refers to, for example, improving the condition of at least one of the symptoms of sepsis, preventing the worsening of at least one sepsis-related symptom, or preventing or limiting the progression of the condition to subsequent stages in the sepsis cascade (e.g., severe sepsis, septic shock, organ damage, etc.). An improvement in at least one of the symptoms of sepsis can be assessed by a physician using routine laboratory tests, assessment of physiological data, (e.g., blood pressure, heart rate, respiratory rate, mental status, urine output, oxygenation, pulmonary artery pressure, pulmonary capillary wedge pressure, or pulmonary artery occlusion pressure, mixed venous oxygen content or saturation, arterial oxygen content or saturation, cardiac output, cardiac index, systemic vascular resistance, pulmonary vascular resistance, oxygen delivery, and oxygen extraction), chest radiograph and other radiological criteria, and standard physical examination of the patient. Determination of therapeutically effective amounts is well within the capability of those skilled in the art.

The decision to begin the therapy for sepsis described herein will be based upon the appearance of the clinical manifestations of sepsis or laboratory tests that show initiation of the sepsis cascade (inclusive of renal complications, coagulation abnormalities, or multiple organ failure). Typical clinical manifestations are described herein above and include fever, chills, tachycardia, tachypnea, altered mental state, hypothermia, hyperthermia, accelerated or repressed breathing or heart rates, increased or decreased white blood cell count, and hypotension. These and other symptoms of sepsis are well known in the art. Alternatively, a physician may choose to initiate the therapeutic methods described herein for a patient at risk of developing sepsis prior to the appearance of clinical symptoms.

A physician of ordinary skill in the art can determine when treatment for sepsis should be initiated and for how long the treatment should continue. Such treatment decisions may be supported by standard clinical laboratory results which monitor the clinical manifestations of sepsis. The methods of the invention may be practiced by continuously or intermittently administering a therapeutically effective dose of the A1 adenosine receptor antagonist in combination with an antibiotic agent for as long as deemed efficacious for the treatment of sepsis. The decision to end therapy by the method of the invention may also be supported by standard clinical laboratory results indicating the disappearance of at least one of the clinical symptoms characteristic of sepsis. The therapy described herein may be restarted upon the return of sepsis.

The combination of the A1 adenosine receptor antagonist and the antibiotic agent is administered at a concentration that is therapeutically effective to treat sepsis. To accomplish this goal, the agents may be formulated using a variety of acceptable excipients known in the art. A1 adenosine receptor antagonists and antibiotic agents may be administered, for example, by injection, either intravenously, intraperitoneally, intramuscularly, or subcutaneously. Methods to accomplish this administration are known to those of ordinary skill in the art. It may also be possible to obtain compositions which may be topically or orally administered, or which may be capable of transmission across mucous membranes.

The amount of a combination of at least one A1 adenosine receptor antagonist and at least one antibiotic agent to be administered is readily determined by one of ordinary skill in the art without undue experimentation. Factors influencing the mode of administration and the respective amount of the combination of agents disclosed herein include, but are not limited to, the severity of the disease, the history of the disease, and the age, height, weight, health, medical history (e.g., existence of other diseases such as diabetes, kidney or liver disease, and other drugs or treatments the patient is currently taking or has taken in the past), and physical condition of the individual undergoing therapy. Similarly, the amount of the combination of therapeutic agents disclosed herein to be administered will be dependent upon the mode of administration and whether the subject will undergo a single dose or multiple doses of these anti-sepsis agents. Generally, a higher dosage of is preferred with increasing weight of the patient undergoing therapy.

The treatment of sepsis described herein can be accomplished with varying doses as well as dosage regimens. Treatment regimens will be based on doses and dosing schedules that maximize therapeutic effects. The therapeutically effective amount of a combination of an A1 adenosine receptor antagonist and an antibiotic agent can be readily determined by one of ordinary skill in the art without undue experimentation. In particular embodiments, the therapeutically effective dose of a combination of an A1 adenosine receptor antagonist and an antibiotic may comprise doses of the individual agents that, when administered alone, would not be therapeutically effective or would be less therapeutically effective than when administered in combination with each other. Thus, when an A1 adenosine receptor antagonist of the invention and an antibiotic agent are administered in combination, a synergistic therapeutic effect may be observed. "Synergistic therapeutic effect" refers to a therapeutic effect observed with a combination of two or more therapies (in this case, the A1 adenosine receptor antagonist and the antibiotic agent) wherein the therapeutic effect (as measured by any of a number of parameters) is greater than the sum of the respective individual therapeutic effects observed with the respective individual therapies. The combination of an A1 adenosine receptor antagonist and an antibiotic agent may produce a synergistic effect that permits a reduction in the dosages of these agents and an improvement of the clinical outcome of the subject being treated. A reduced dose of the A1 adenosine receptor antagonist and the antibiotic agent may in turn reduce unwanted side effects associated with each agent.

In some embodiments of the invention, the method comprises administration of multiple doses of an A1 adenosine receptor antagonist in combination with multiple doses of an antibiotic agent. The method may comprise administration of 1, 2, 3, 4, 5, 6, 7, 8, 9, 10, 15, 20, 25, 30, 35, 40, or more therapeutically effective doses of a pharmaceutical composition comprising either an A1 adenosine receptor antagonist or an antibiotic agent, or both. The frequency and duration of administration of multiple doses of the pharmaceutical compositions can be readily determined by one of skill in the art without undue experimentation. Moreover, treatment of a subject with a therapeutically effective amount of a combination of an A1 adenosine receptor antagonist and an antibiotic agent can include a single treatment or can include a series of treatments. It will also be appreciated that the effective dosage of an A1 adenosine receptor antagonist or an antibiotic agent used for treatment may increase or decrease over the course of a particular treatment. Changes in dosage may result and become apparent from the results of diagnostic assays known in the art.

Many of the A1 adenosine receptor antagonist compounds of the present invention can be provided as solvates, hydrates, and salts with pharmaceutically compatible counterions. Such pharmaceutically acceptable base addition salts are those salts that retain the biological effectiveness and properties of the free acids, and that are obtained by reaction with suitable inorganic or organic bases. The A1 adenosine receptor antagonists of the invention may form pharmaceutically acceptable salts with both organic and inorganic acids and bases. Exemplary weak organic acids for salt formation include but are not limited to acetic acid, beta-alanine, dl-alanine, D-alanine, L-alanine, formic acid, propanoic acid, butyric acid, palmetic acid, oleic acid, sebacic acid, cinnamic acid, adipic acid, citric acid, ascorbic acid (vitamin C), lactic acid, malic acid, maleic acid, fumaric acid, tartaric acid, dl-glutamic acid, D-glutamic acid, L-glutamic acid, dl-aspartic acid, D-aspartic acid, L-aspartic acid, glycine, succinic acid, glutaric acid, gluconic acid, benzoic acid, p-chlorobenzoic acid, p-hydroxybenzoic acid, p-methoxybenzoic acid, o-hydroxybenzoic acid (salicylic acid), 1-hydroxy-2-naphthoic acid, 3-hydroxy-2-naphthoic acid, and the like. Strong organic acids that may be used for salt formation include, for example, benzenesulfonic acid, p-toluenesulfonic acid, m-nitrobenzenesulfonic acid, methanesulfonic acid, ethanesulfonic acid, 1-naphthalenesulfonic acid, 2-naphthalenesulfonic acid, laurylsulfonic acid, and the like. Examples of strong inorganic acids for salt formation include hydrochloric acid, hydrobromic acid, hydroiodic acid, sulfuric acid, phosphoric acid, nitric acid, sodium bisulfate, potassium bisulfate, sodium hydrogen phosphate, potassium hydrogen phosphate, boric acid, and the like. In a particular embodiment of the invention, L-97-1 xinafoate salt is formed with 1-hydroxy-2-naphthoic acid (i.e., xinafoic acid).

In particular aspects of the invention, a xinafoate salt (1-hydoxy-2-napthoic acid) of an A1 adenosine receptor antagonist is administered in combination with an antibiotic agent to treat or prevent sepsis in a subject. Xinafoate salts, such as salmeterol xinafoate, are known and have been synthesized in the art. See, for example, Merck Index, supra, and U.S. Pat. No. 4,992,474, both of which are herein incorporated by reference in their entirety. Because xinafoate salts are known to be largely insoluble and to exhibit reduced oral absorption, such salts may be particularly potent, safe, and efficacious when administered by pulmonary inhalation. Inhalational therapy with a xinafoate salt of an A1 adenosine receptor antagonist of the invention may minimize negative systemic effects associated with the antagonist agent.

The A1 adenosine receptor antagonist and antibiotic agent are typically provided by standard technique within a pharmaceutically acceptable buffer; for example, sterile saline, sterile buffered water, propylene glycol, combinations of the foregoing, etc. The A1 adenosine receptor antagonist and antibiotic agent can be formulated in separate pharmaceutical compositions, or can be formulated within a single pharmaceutical composition for simultaneous administration. Methods for preparing parenterally administrable agents are described in *Remington's Pharmaceutical Sciences* (18$^{th}$ ed.; Mack Publishing Company, Eaton, Pa., 1990), herein incorporated by reference.

The A1 adenosine receptor antagonists and antibiotic agents of the invention can be administered alone, but may also be administered in admixture with a pharmaceutically acceptable carrier selected with regard to the intended route of administration and pharmaceutical practice. Thus, a pharmaceutical composition of the invention is formulated to be compatible with its intended route of administration. Examples of possible routes of administration include parenteral, (e.g., intravenous (IV), intramuscular (IM), intradermal, subcutaneous (SC), or infusion), oral, pulmonary (e.g., inhalation), nasal, transdermal (topical), transmucosal, and rectal administration. A "pharmaceutically acceptable carrier" refers to a carrier that is conventionally used in the art to facilitate the storage, administration, or the therapeutic effect of the active ingredient. A suitable carrier may also reduce any undesirable side effects of the A1 adenosine receptor antagonist or the antibiotic agent. It should not produce significant local or systemic adverse effects in recipients at the dosages and concentrations employed for treatment. Pharmaceutically acceptable carriers of the invention may further comprise surfactants, such as those disclosed in U.S. Pat. Nos. 6,652,837 and 6,613,307, which are herein incorporated by reference in their entirety. Methods for formulating pharmaceutical compositions are generally known in the art. A thorough discussion of formulation and selection of pharmaceutical acceptable carriers, stabilizers, and isomolytes can be found in *Remington's Pharmaceutical Sciences* (18$^{th}$ ed.; Mack Publishing Company, Eaton, Pa., 1990), herein incorporated by reference.

When a composition of the invention is administered by intravenous, intradermal, or subcutaneous injection, the composition is in the form of a pyrogen-free, parenterally acceptable aqueous solution. The preparation of such parenterally acceptable solutions, having due regard to pH, isotonicity, stability, and the like, is well within the skill in the art. Solutions or suspensions used for parenteral, intradermal, subcutaneous, or intravenous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, multiple dose vials made of glass or plastic, or plastic bags of intravenous solutions, e.g. dextrose, ringers lactate or normal saline.

The A1 adenosine receptor antagonists of the invention can be formulated for parenteral administration by injection, e.g., by bolus injection or continuous infusion. Formulations for injection can be presented in unit dosage form, e.g., in ampoules or in multidose containers, with an added preservative. The compositions can take such forms as suspensions, solutions, or emulsions in oily or aqueous vehicles, and can contain formulatory agents such as suspending, stabilizing, and/or dispersing agents.

For oral administration, the A1 adenosine receptor antagonists can be formulated by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, A1 adenosine receptor antagonists of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch. Methods and devices for administering compositions via pulmonary inhalation and for producing particles suitable for such administration are disclosed in the art. See, for example, U.S. Pat. Nos. 6,221,338, 6,475,523, 6,521,260, 6,582,678, 6,941,948, 6,948,496, 6,989,155; U.S. Patent Application Publication Nos. 2003/0170183, 2003/0202944, 2005/0013862, 2005/0152849, 2005/0158394, 2005/0205083, and 2006/0029552; all of which are herein incorporated by reference in their entirety.

The exact formulation, route of administration, and dosage of the A1 adenosine receptor antagonist and antibiotic agent can chosen by the individual physician in view of the patient's condition. Dosage amount and dosing intervals can be adjusted individually to provide plasma levels of the A1 adenosine receptor antagonist and antibiotic agent that are sufficient to maintain positive therapeutic effects.

One of skill in the art will appreciate that the methods for treating sepsis disclosed herein can be combined with any other therapy for sepsis. Such therapies include but are not limited to fluid therapy, vasopressor therapy, inotropic therapy, steroid administration, blood product administration, mechanical ventilation, glucose control, and renal replacement. See, for example, Dellinger et al. (2004) Crit. Care Med. 32(3):858-873, which is herein incorporated by reference.

The present invention also provides for the use of an A1 adenosine receptor antagonist in the manufacture of a medicament for treating a subject for sepsis, wherein the medicament is coordinated with treatment using an antibiotic agent. By "coordinated" is intended that the medicament comprising the A1 adenosine receptor antagonist is to be used either prior to, during, or after treatment of the subject using an antibiotic agent. "Treatment" in the context of coordinated use of a medicament comprising an A1 adenosine receptor antagonist described herein with one or more antibiotic agents is herein defined as the application or administration of the medicament or of the antibiotic agent to a subject, where the subject has sepsis, a symptom associated with sepsis, or a predisposition toward development of sepsis, where the purpose is to cure, heal, alleviate, relieve, alter, remedy, ameliorate, improve, or affect the septic condition, any associated symptoms of sepsis, or the predisposition toward the development of sepsis.

The present invention also provides for the use of a synergistic combination of an A1 adenosine receptor antagonist in the manufacture of a medicament for treating a subject for sepsis, wherein the medicament is coordinated with treatment using an antibiotic agent. By "synergistic combination" is intended that the medicament comprising an amount of the A1 adenosine receptor antagonist provides for a synergistic therapeutic effect when the medicament is coordinated with treatment using an antibiotic agent in the manner set forth herein above. As indicated above, "synergistic therapeutic effect" refers to a therapeutic effect observed with a combination of two or more therapies (in this case, the A1 adenosine receptor antagonist and the antibiotic agent) wherein the therapeutic effect (as measured by any of a number of parameters) is greater than the sum of the respective individual therapeutic effects observed with the respective individual therapies.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

EXPERIMENTAL

Example 1

L-97-1 Pharmacological and Pharmacokinetic Studies

A. In vitro Pharmacology Studies

L-97-1 is a small molecule (MW 519) and is water-soluble ($10^{-3}$ M). L-97-1 is an analog of the known adenosine receptor antagonist bamiphylline. In vitro pharmacology studies (i.e., radioligand binding assays) were performed and the results support that L-97-1 has a high affinity for the human A1 AR (0.58 µM) and is highly selective for the human A1 AR versus human A2a and A2b ARs and the rat A3 AR (see Tables 1 and 2 below). In these studies, the affinity of L-97-1 for the human A1 AR was determined to be approximately 3-10 times that of bamiphylline (Table 1). L-97-1 was more selective for the human A1 AR than bamiphylline (Table 2). Bamiphylline bound to the human A2a AR (27 µM). L-97-1, however, did not bind to the human A2a AR ($\leqq$100 µM). Neither L-97-1 ($\leqq$100 µM) nor bamiphylline ($\leqq$100 µM) bound to the human A2b AR. The affinity of L-97-1 for the human A1 AR was close to the affinity of LPS (i.e., endotoxin) for the human A1 AR (Table 1).

TABLE 1

Affinities of L-97-1 and other AR ligands for Human A1 AR

| Ligand | Human $A_1$ ($^{125}$I-BWA844U) | | | | Human $A_1$ ($^3$H-DPCPX) | | | |
|---|---|---|---|---|---|---|---|---|
| | $IC_{50}$ (µM) | $K_i$ (µM) | $IC_{50}$ (µg/ml) | N | $IC_{50}$ (µM) | $K_i$ (µM) | $IC_{50}$ (µg/ml) | N |
| L-97-1 | 2.077 ± 0.712 | 1.13 ± 0.39 | 1.077 ± 0.369 | 3 | 1.421 ± 0.567 | 0.580 ± 0.330 | 0.737 ± 0.294 | 4 |
| Bamiphylline | 20.150 ± 12.65 | 11.05 ± 6.95 | 8.483 ± 5.325 | 2 | 3.770 ± 0.964 | 1.927 ± 0.517 | 1.587 ± 0.406 | 3 |

TABLE 1-continued

Affinities of L-97-1 and other AR ligands for Human A1 AR

| | Human A$_1$ ($^{125}$I-BWA844U) | | | | Human A$_1$ ($^3$H-DPCPX) | | | |
|---|---|---|---|---|---|---|---|---|
| Ligand | IC$_{50}$ (μM) | K$_i$ (μM) | IC$_{50}$ (μg/ml) | N | IC$_{50}$ (μM) | K$_i$ (μM) | IC$_{50}$ (μg/ml) | N |
| DPCPX | 13.2 ± 1.2 | 7.19 ± 0.654 | 4.013 ± 0.365 | 3 | 0.076 ± 0.036 | 0.038 ± 0.018 | 0.023 ± 0.011 | 4 |
| CCPA | | | | | 0.034 ± 0.023 | 0.017 ± 0.012 | 0.013 ± 0.009 | 2 |
| LPS | | | 1.095 ± 0.695 | 2 | | | 0.225 ± 0.046 | 2 |

TABLE 2

Affinities of L-97-1 and other AR ligands for Human A2a, A2b, and Rat AR subtypes

| | Human A$_{2a}$ ($^3$H-CGS21680) | | | Human A$_{2b}$ ($^3$H-DPCPX) | | | Rat A$_3$ ($^{125}$I-AB-MECA) | | |
|---|---|---|---|---|---|---|---|---|---|
| Ligand | IC$_{50}$ (μM) | K$_i$ (μM) | N | IC$_{50}$ (μM) | K$_i$ (μM) | N | IC$_{50}$ (μM) | K$_i$ (μM) | N |
| L-97-1 | >100 | | 3 | >100 | | 3 | 67.33 ± 28.76 | | 3 |
| Bamiphylline | 26.6 ± 7.9 | 12.92 ± 3.85 | 2 | >100 | | 3 | 36.6 ± 4.00 | 17.55 ± 1.95 | 2 |
| DPCPX | | | | 0.219 ± 0.065 | 0.12 ± 0.035 | 3 | | | |
| CGS-21680 | 0.32 ± 0.215 | 0.158 ± 0.106 | 3 | | | | | | |
| Cl-IB-MECA | | | | | | | 0.19 nM | 0.09 nM | 1 |

Additional in vitro pharmacology studies were performed by Dr. Gary Stiles (Duke University Medical Center) under a Sponsored Research Agreement and also by two CROs that specialize in receptor radioligand binding and functional assays, NovaScreen (Hanover, Md.) and CEREP (Celle l'Evescault, France). The affinities of L-97-1 and bamiphylline for the recombinant human A1 AR were 5.6 μM and 40 μM, respectively. There was no binding of L-97-1 or bamiphylline to recombinant human A2 or A3 ARs. The differences in the affinities of bamiphylline to the human A2 AR in the experiments described above versus Dr. Stiles' experiments are most likely explained by the differences in the affinities of the two different A2 radioligands used by the two different laboratories. The A2 AR radioligand used by Dr. Stiles was [$^{125}$I]ZM 241835. This ligand binds to A2b ARs. See Ongini et al. (2001) Farmaco 56:87-90. The A2 AR radioligand used in the above experiments was [$^3$H] CGS21680, which has a high affinity (0.16 μM) for the human A2a AR.

At NovaScreen (Hanover, Md.), L-97-1 was screened through other receptor radioligand binding assays. There was no binding of L-97-1 to rat adrenergic, alpha 1 and alpha 2, peripheral benzodiazepine, non-selective dopamine, glutamate (AMPA, kainate, NMDA agonist, and glycine NMDA sites), strychnine-sensitive glycine, H1 histamine, H2 histamine, and H3 histamine, non-selective central muscarinic, non-selective peripheral muscarinic, non-selective serotonin, and non-selective opiate receptors.

The effect of L-97-1, bamiphylline and theophylline on human PDE enzymes II, III, IV, and V was determined in the laboratory of CEREP. The data from this study is provided in the Table below. As opposed to bamiphylline and theophylline, even at a high concentration, L-97-1 (100 μM) did not inhibit human PDE enzymes.

TABLE 3

Effects of Adenosine Receptor Antagonists on PDE's

| | L-97-1 | Theophylline | Bamiphylline | Reference compounds | | |
|---|---|---|---|---|---|---|
| Assays | 100 μM | 100 μM | 100 μM | | IC$_{50}$ (μM) | (nH) |
| Phosphodiesterase II (h) | — | 19 | 48 | EHNA | 4.7 | (0.7) |
| Phosphodiesterase III (h) | — | 28 | 52 | milrinone | 0.39 | (0.8) |
| Phosphodiesterase IV (h) | — | 21 | 46 | rolipram | 0.21 | (0.6) |
| Phosphodiesterase V (h) | — | — | 25 | dipyridamole | 0.80 | (1.2) |

For the test compounds, the results are expressed as a percent inhibition of control activity (mean values; n = 2).
The symbol — indicates an inhibition of less than 10%.

B. Single Dose Pharmacokinetic Studies in Rats Performed by SRI

Early rat pharmacokinetic (PK) studies were performed by SRI International Toxicology Laboratory (Menlo Park, CA). These early PK studies in rats supported that L-97-1 has a short half-life (approximately 0.5 hrs.) in rats when administered intravenously (i.v.). The protocol for dosing rats in these early PK/toxicology studies at SRI was as follows: Rats (0.3 kg) were administered L-97-1 (0.5, 1.0, and 10.0 mg/kg, IV)

and plasma samples for L-97-1 were obtained at 1 and 3 hours from 3 animals for each time point. The bioanalytical method to measure L-97-1 in plasma was developed by Oneida Research Services Prevalere Life Sciences (Whitesboro, NY). Prevalere validated L-97-1 in rat plasma. All doses were well-tolerated by rats, with no clinical observations noted within 4 hours of drug administration. At 0.5 mg/kg i.v., estimated plasma concentrations of L-97-1 were between 3 and 6 ng/ml after 1 hour, but were below the limit of quantitation for the LC/MS assay (1 ng/ml) after 3 hours. At 5 and 10 mg/kg i.v., mean plasma concentrations at 1 hour post-dose were 98 and 167 ng/ml, respectively. Extrapolating from the plasma concentrations at the top two doses, the plasma half-life for L-97-1 was approximately 30 minutes after i.v. administration, suggesting that the drug may be rapidly metabolized in the rat.

C. Single Dose Animal Toxicology Studies Performed by CTBR

1. Acute Dose Toxicity

The following acute dose toxicity studies were performed by CTBR (Quebec, Canada) and plasma levels were analyzed by Prevalere Life Sciences, Inc. (Whitesboro, N.Y.). Summaries are provided from reports provided by CTBR and Prevalere Life Sciences.

2. Acute oral/IV (Single Dose) Toxicity Study (with 14 Day Observation) in Rats

The purpose of this study was to investigate the potential toxicity of L-97-1 following a single oral (gavage) or a single intravenous injection administration to the rat followed by a 14-day observation period. The design of the study is summarized in the table below:

TABLE 4

Study Design

| Group | Designation | Dose Level* (mg/kg/day) | Number of Animals | | | |
|---|---|---|---|---|---|---|
| | | | Main Study | | Toxicokinetic Study | |
| | | | Males | Females | Males | Females |
| 1 | Vehicle control | 0 | 5 | 5 | — | — |
| 2 | L-97-1 | 10 | 5 | 5 | 6 | 6 |
| 3 | L-97-1 | 50 | 5 | 5 | 6 | 6 |
| 4 | L-97-1 | 200 | 5 | 5 | 6 | 6 |
| 5 | L-97-1 (IV) | 10 | 5 | 5 | 6 | 6 |

*Free base adjusted for molecular weight of salt (correction factor of 1.14)

Results

No mortalities and no compound-related clinical signs were observed. Moreover, there were no compound-related effects on body weight, body weight gain or food consumption. No changes were noted for any hematology, clinical chemistry or urinalysis parameters examined indicative of a compound-related effect. No test article-related gross pathological findings were noted.

Conclusions

L-97-1 administered as a single oral (gavage) dose up to 200 mg/kg or intravenous injection at 10 mg/kg was well tolerated.

3. Toxicokinetics

The objective of this study was to determine plasma exposure to L-97-1 following a single IV dose of 10 mg/kg and after a single oral dose of 10, 50, or 200 mg/kg of L-97-1 in healthy male and female rats. Blood samples were obtained from 3 male and 3 female animals per active dose group on Day 1 prior to dose administration, and at 0.5, 1, 2, 4, and 6 hours after dosing in the 10 and 50 mg/kg Dose Groups. In the 200 mg/kg Dose Group, blood samples were obtained prior to dose administration, and at 0.5, 1, 4, 6, and 8 hours. Summary of the results is as follows:

TABLE 5

SUMMARY OF PLASMA L-97-1 Cmax VALUES AND DOSE-NORMALIZED Cmax VALUES FOLLOWING ORAL ADMINISTRATION (DAY 1)

| | Combined (Males and Females) | |
|---|---|---|
| | Cmax | Cmax/Dose |
| 10 mg/kg | 71.6 | 7.16 |
| 50 mg/kg | 531.8 | 10.6 |
| 200 mg/kg | 1644.5 | 8.22 |

TABLE 6

SUMMARY OF PLASMA L-97-1 Cmax VALUES AND DOSE-NORMALIZED Cmax VALUES FOLLOWING INTRAVENOUS ADMINISTRATION (DAY 1)

| | Combined (Males and Females) | |
|---|---|---|
| | Cmax | Cmax/Dose |
| 10 mg/kg | 1152.8 | 11.5 |

Conclusions

All animals were exposed to L-97-1 after oral and intravenous administration and plasma L-97-1 concentrations were in the ng/ml concentration range for at least 6 hours.

There were no substantial differences in plasma L-97-1 concentrations between male and female animals.

Approximate dose-proportionality was observed between administered dose and Cmax following single-dose oral administration in the combined group of male and female rats.

A nonlinear relationship was observed between plasma L-97-1 exposure (AUC0-$_{0-\infty}$) and dose following single-dose oral administration of 10, 50 and 200 mg/kg L-97-1 in the combined group of male and female rats.

The nonlinear plasma exposure to L-97-1 was, in part, related to dose-dependent changes in L-97-1 disposition or distribution at these high doses. The apparent half-life values obtained from the composite plasma concentration versus time data were 2.11 hr, 3.52 hr and 11.6 hr following administration of 10, 50, and 200 mg/kg oral doses of L-97-1, respectively. The half-life value following administration of an L-97-1 10 mg/kg intravenous dose was 1 hour.

4. Maximum Tolerated Single Dose (Oral) in Rats

This study was conducted to investigate the potential acute toxicity of L-97-1 following a single oral administration to the rat followed by a 48-hour observation period. Animals were weighed and randomly assigned to the treatment groups as follows:

TABLE 7

Treatment Groups

| Group No. Identification | Dose Level (mg/kg)* | Dose Volume (mL/kg) | Animal Number Males | Females |
|---|---|---|---|---|
| Group 1 | 1000 | 5 | 1001-1002 | 1501-1502 |
| Group 2 | 2000@ | 5 | 2001-2002 | 2501-2502 |
| Group 3 | 1000@ | 5 | 3001 | 3501 |

Group 1 was dosed at 1000 mg/kg followed by a 48-hour observation period. No clinical signs of toxicity were noted. As such, Group 2 animals were dosed at 2000 mg/kg followed by a 48-hour observation period. No clinical signs of toxicity were noted at 2000 mg/kg. It was decided to dose Group 3 animals at 1000 mg/kg and collect blood samples for toxicokinetic evaluation. Results of toxicokinetic studies are as follows:

TABLE 8

Results of Toxicokinetic Studies

| Animal # | Day | Timepoint | Filename | Conc. (ng/mL) |
|---|---|---|---|---|
| 3001 | 1 | 15 min post RX | 2c1a | 3755 |
| 3001 | 1 | 30 min post RX | 2c2a | 3056 |
| 3001 | 1 | 1 hr post RX | 2c3a | 1950 |
| 3501 | 1 | 15 min post RX | 2c4a | 1093 |
| 3501 | 1 | 30 min post RX | 2c5a | 2004 |
| 3501 | 1 | 1 hr post RX | 2c6a | 4723 |

Conclusions from Acute Dose Toxicity/Pharmacokinetic Preclinical Studies:

In rats, the maximum tolerated dose for L-97-1 is greater than 2000 mg/kg oral with a Cmax of approximately 4000 ng/ml; Cmax is 1645 ng/ml at 200 mg/kg oral; Cmax is 1153 ng/ml at 10 mg/kg IV.

Example 2

Evaluation of L-97-1 and Antibiotic Combination Therapy in Rat Model of Gram-Negative Sensis Studies will be undertaken to determine if L-97-1 is an effective adjuvant therapy to antibiotics for the treatment of sepsis and early treatment of endotoxin- induced acute lung injury (ALI) and improves outcome and mortality (versus antibiotics alone). In a rat cecal ligation perforation (CLP) model of Gram-negative septicemia and endotoxemia, the effect of L-97-1 (and L-97-1 plus antibiotics, ampillicin plus gentamicin) on acute lung injury (ALI) at 24 and 72 hours and on mortality at 7 days following CLP will be investigated.

In the rat CLP model of septicemia and endotoxemia, at 5 hours post-CLP, endotoxin levels are increased and 60% of rats have blood cultures that grow Gram-negative rods (*Escherichia coli* and *Klebsiella pneumoniae*). Alexander et al. (1991) *J Clin. Invest.* 88:34-39. At 20 hours post-CLP all rats have positive blood cultures. Animals develop clinical signs of sepsis—decreased physical activity, piloerection, cessation of grooming behavior, glazed eyes with crusting exudates, tachypnea, and reduced urinary output—at 6-12 hours following CLP. Hubert-Lang et al. (2001) *FASEB J* 15:568-570; Stockwell et al. (1994) *Circ. Shock* 42:68-75; and Schneidkraut et al. (1993) *Prostaglandins* 45:323-334. The mortality rate is 50-80% with deaths usually occurring 24-72 hours post-CLP. See generally Stockwell, supra; Schneidkraut, supra; Toda et al. (1993) *Stem Cells* 11:228-234; Villar et al. (1994) *Crit. Care Med.* 22:914-921; Parker et al. (2001) *Brit. J Surg.* 88:22-30; and Murata et al. (1992) *Am. Rev. Resp. Dis.* 146:1048-1053. Treatment with antibiotics [ampicillin (100 mg/kg) plus gentamicin (4 mg/kg), i.p.] increases the survival rate of animals at 96 hours following CLP from 23% to 75%. Stockwell, supra. In previous studies, animals that survived at 96 hours appeared healthy. This model of peritonitis closely resembles the physiological changes in humans with sepsis and pathological changes of ALI comparable to those of humans dying from early ALI and sepsis. See Villar, supra, and Parker, supra.

Protocol for Cecal Ligation-and-Perforation (CLP) Model of Sepsis-Induced AL1:

Surgical procedures and animal care are in compliance with the guidelines established by the Animal Use Committee of the University of Loyola of Chicago Stritch School of Medicine. Male Sprague-Dawley rats (200-300 g) receive an intraperitoneal (ip) injection of sodium pentobarbital (50 mg/kg) prior to surgery. Surgery is performed after overnight fasting through a 2 cm midline abdominal incision using aseptic techniques. During surgery the cecum is ligated below the ileocecal valve with 3-0 silk. Toda et al. (1993) *Stem Cells* 11:228-234. Two perforations (1 cm apart) will be made in the cecum with an 18-guage needle on its antimesenteric surface. Before the bowel is inserted back into the abdomen and the incision closed, the cecum is gently squeezed until feces extrudes out. Post-operative fluid resuscitation is a 20 ml subcutaneous injection of saline. During surgery rats will have a catheter surgically implanted intravenously and sutured for continuous infusion of L-97-1 to begin after surgery according to the treatment protocols below.

Rats are treated with either vehicle or L-97-1 as a continuous intravenous infusion following CLP and catheter placement according to the treatment protocols below. This infusion is maintained for 8 hours. For continuous intravenous infusion of L-97-1, rats receive a harness to ensure the catheter remains in place. The catheter itself is attached to a swivel to allow the animals free movement in the cage. L-97-1 or vehicle will infuse through the catheter for 8 hours by connection to a Harvard® pump apparatus. Monitoring of animals will continue until they are fully conscious and moving after surgery. The rats receive further postoperative monitoring every 8 hours. Rats are allowed free access to food and water following surgery.

Treatment Protocol for CLP-Induced ALI Experiments:

TABLE 9

Evaluation of Acute Lung Injury (ALI) (24 and 72 hours post CLP)*; Evaluation of Mortality (0 hours to 7 days post CLP)

| Group | Treatment |
|---|---|
| 1 | Control Injury + No treatment whatsoever |
| 2 | Sham: Injury + Vehicle |

TABLE 9-continued

Evaluation of Acute Lung Injury (ALI) (24 and 72 hours post CLP)*; Evaluation of Mortality (0 hours to 7 days post CLP)

| Group | Treatment |
|---|---|
| 3 | L-97-1 (5 mg/kg/hour) immediately post CLP + Injury |
| 4 | L-97-1 (10 mg/kg/hour) immediately post CLP + Injury |
| 5 | L-97-1 (15 mg/kg/hour) immediately post CLP + Injury |
| 6 | Amipicillin (100 mg/kg i.p.) plus Gentamicin (4 mg/kg, i.p.) immediately post CLP + Injury |
| 7 | L-97-1 (5 mg/kg/hour) immediately post CLP + Amipicillin (100 mg/kg i.p.) plus Gentamicin (4 mg/kg, i.p.) immediately post CLP + Injury I |
| 8 | L-97-1 (10 mg/kg/hour) immediately post CLP + Amipicillin (100 mg/kg i.p.) plus Gentamicin (4 mg/kg, i.p.) immediately post CLP + Injury |
| 9 | L-97-1 (15 mg/kg/hour) immediately post CLP + Amipicillin (100 mg/kg i.p.) plus Gentamicin (4 mg/kg, i.p.) immediately post CLP + Injury |
| 10 | L-97-1 (15 mg/kg/hour) 6 hours post CLP + Injury |
| 11 | L-97-1 (15 mg/kg/hour) 12 hours post CLP + Injury |
| 12 | Amipicillin (100 mg/kg i.p.) plus Gentamicin (4 mg/kg, i.p.) 6 hours post CLP + Injury |
| 13 | Amipicillin (100 mg/kg i.p.) plus Gentamicin (4 mg/kg, i.p.) 12 hours post CLP + Injury |
| 14 | L-97-1 (15 mg/kg/hour) 6 hours post CLP + Amipicillin (100 mg/kg i.p.) plus Gentamicin (4 mg/kg, i.p.) immediately post CLP + Injury |
| 15 | L-97-1 (15 mg/kg/hour) 12 hours post CLP + Amipicillin (100 mg/kg i.p.) plus Gentamicin (4 mg/kg, i.p.) immediately post CLP + Injury |

*Quantitation of ALI by analysis of lung specimens by histopathology and bronchoalveolar lavage (BAL) for protein content; total cell count; differential cell count; N = 10 rats per group; Total rats (15 groups × 10 rats) × 3 time points (24 and 72 hrs and 7 days) = 450 rats Treatment with L-97-1 will begin according to the treatment protocols above and continue (as a single, continuous intravenous infusion) for 8 hours.

Animals are sacrificed at 24 hours following CLP in the 24 hour groups or at 72 hours in the 72 hour groups with an overdose of sodium pentobarbital (150 mg/kg, i.p.).

ALI is evaluated at 24 and 72 hrs following CLP. Lung specimens are obtained for histopathology and BAL samples are obtained for cell counts and total protein levels.

Mortality is evaluated at 7 days for those animals that are not sacrificed for ALI evaluation at 24 hours and 72 hours following CLP.

Bronchoalveolar Lavage (BAL): Protocol and Analysis of Samples

Bronchoalveolar lavage (BAL) is performed on rats at 24 and 72 hours following CLP. BAL is performed in five control animals (no injury and no treatment). The lungs are lavaged 5 times with 0.035 ml/g saline immediately following sacrifice of the animal. The BAL fluid is analyzed for protein concentration, total cell count, and differential cell count. BAL fluid will be centrifuged at 150×g for 10 minutes to separate cells. Cell pellets will be resuspended in PBS and total cell numbers will be quantified using trypan blue stain, a haemocytometer and light microscopy. Cytospin preparations are prepared with a Cytospin 4 ™ (Thermo Shandon, Inc). Diff-Quick stain and light microscopy will enable a differential count of all cell samples. A minimum of 500 cells/sample will be visualized and categorized for different populations of leukocytes. The colorimetric, BCA protein reagent assay protocol (Pierce Endogen Inc), will enable all samples to be assayed for total protein concentration.

Histopathology

After the collection of BAL fluid, lungs will be prepared for analysis of lung injury by histopathology. Lungs from each animal will be sampled in 8 random locations. The samples will be immersed in 10% neutral buffered formalin fixative. Mounted sections (5 µm) of processed and paraffm-embedded tissue samples will be stained with hematoxylin and eosin. A double-blind system using the following parameters: percent alveoli containing one or more neutrophils (PMNs), macrophages, or red blood cells (RBCs) (% alv); average number of each cell type per 100 alveoli (no./alv); % alveoli containing two or more inflammatory cells or RBCs, or edematous fluid (% injured alveoli). These parameters are based on 480 alveoli per rat, randomly selected in groups of 8 per field, using a 40× objective. This method of quantifying lung injury is previously described. Murata et al. (1992) *Am. Rev. Resp. Dis.* 146:1048-1053.

Lung specimens are obtained from all groups of rats including 5 normal controls (no injury and no treatment). Lung specimens will be obtained for histopathology in two normal controls without BAL to ensure that BAL does not affect histopathology of lung specimens. If it is determined that BAL affects histopathology, 5 animals will be used for BAL studies without histopathology and 5 animals will be used for histopathology without BAL from each group of 10 animals as described in the table above to evaluate ALI.

Kinetics of L-97-1 and LPS in Plasma

Healthy rats and rats with the CLP model of ALI will also be used to assess the kinetics of L-97-1 and endotoxin (LPS) in plasma. The kinetics of L-97-1 in the plasma of healthy rats will be compared with that of rats that have undergone the CLP procedure. The kinetics of L-97-1 will also be compared in CLP rats that have been treated with and without antibiotics, particularly ampicillin and gentamicin. Finally, it will be determined if the development of ALI correlates with increasing plasma levels of endotoxin.

For each of three groups (controls, CLP, and CLP plus ampicillin and gentamicin), 4 rats will be bled at each of 9 time points. One rat will be bled for a maximum of 4 bleeds per rat during the 72 hour study at 0, 1, 2, 4, 8, 16, 24, 48, and 72 hours. The dose of L-97-1 for these kinetic studies will be determined from the treatment groups with L-97-1 in the CLP groups described above. L-97-1 will be infused 8 hours a day as continuous infusion for 72 hours. Plasma samples (2 ml/sample) obtained from both groups (healthy, controls, CLP, and CLP plus ampicillin and gentamicin) at times 0, 1, 2, 4, 8, 16, 24, 48, 72 hours will be analyzed for L-97-1 and endotoxin. L-97-1 plasma levels will be assayed by Oneida Research Services/Prevalere Life Sciences and endotoxin levels will be analyzed by ELISA at Endacea, Inc. A total of 27 rats will be needed for these kinetic studies (4 rats per time point×9 time points×3 groups (controls, CLP, CLP plus ampicillin and gentamicin) with each rat bled four times.

Statistical Analysis

Significance of variance within the group and differences between groups will be analyzed using one-way or multivariate ANOVA with Bonnferoni correction and/or Newman-Keuls tests for multiple comparisons. Assessments of significance of relationships between dependent (measured) and independent variables, when required, will be made using regression analyses and determinations of Correlation Coefficients. Null hypothesis, for intra-group variance/inter-group difference(s), or relationships between dependent and independent variables, will be rejected at P values less than 0.05. Analysis of lung specimens for histopathology: percentage data for each rat is arcsin transformed and group means are analyzed using ANOVA and Bonferroni range test. The level of significance is set at $P<0.05$. For the seven day mortality studies, the survival curves for each group will be compared to either control or antibiotics alone using the Mantel-Haenszel logrank test to determine the one-tail P-value. The level of significance is set at $P<0.05$. The seven day mortality data will be plotted as survival curves using GraphPad Prism, version 4.01 (GraphPad Software, Inc., San Diego, Calif.). Data will be analyzed using the product limit method of Kaplan and Meier to determine median survival time for each group.

Example 3

Seven Day Survival Studies in Rat Model for Sepsis

Protocol for Cecal Ligation-and-Perforation (CLP) Model of Sepsis

Male Sprague-Dawley rats (200-300 g) received an intraperitoneal (ip) injection of sodium pentobarbital (50 mg/kg) prior to surgery. Surgery was performed after overnight fasting through a 2 cm midline abdominal incision using aseptic techniques. During surgery the cecum was ligated below the ileocecal valve with 3-0 silk. Two perforations (I cm apart) were made in the cecum with an 18-guage needle on it's antimesenteric surface. Before the bowel was inserted back into the abdomen and the incision closed, the cecum was gently squeezed until feces extrudes out. Post-operative fluid resuscitation was a 20 ml subcutaneous injection of saline. During surgery rats had a catheter surgically implanted intravenously and were sutured for continuous infusion of L-97-1 to begin after surgery according to the treatment protocols below.

Protocol for Treatment with L-97-1 with and without Antibiotics Following CLP: Determination of Seven day Mortality Rats were treated with either vehicle or L-97-1 as a single 8 hour continuous intravenous infusion following CLP according to the treatment protocols below. 8-12 rats per treatment group were used. The infusion of vehicle or L-97-1 was maintained for 8 hours. For continuous intravenous infusion of vehicle or L-97-1, rats received a harness to ensure the catheter remains in place. The catheter itself was attached to a swivel to allow the animals free movement in the cage. L-97-1 or vehicle was infused through the catheter for 8 hours by connection to a Harvard® pump apparatus. Antibiotics, ampicillin or gentamicin were administered by intraperitoneal (i.p) injection immediately following CLP. Antibiotic treatments were not repeated. Monitoring of animals continued until they were fully conscious and moving after surgery. The rats received further postoperative monitoring every 8 hours. Rats were allowed free access to food and water following surgery. Seven day mortality was determined.

TABLE 10

Treatment Protocols

| Group | Treatment |
|---|---|
| 1 | Control Injury + No treatment whatsoever |
| 2 | L-97-1 (5 mg/kg/hour) immediately post CLP + Injury |
| 3 | L-97-1 (10 mg/kg/hour) immediately post CLP + Injury |
| 4 | L-97-1 (15 mg/kg/hour) immediately post CLP + Injury |
| 5 | Amipicillin (100 mg/kg i.p.) plus Gentamicin (4 mg/kg, i.p.) immediately post CLP + Injury |
| 6 | L-97-1 (5 mg/kg/hour) immediately post CLP + Amipicillin (100 mg/kg i.p.) plus Gentamicin (4 mg/kg, i.p.) immediately post CLP + Injury I |
| 7 | L-97-1 (10 mg/kg/hour) immediately post CLP + Amipicillin (100 mg/kg i.p.) plus Gentamicin (4 mg/kg, i.p.) immediately post CLP + Injury |
| 8 | L-97-1 (15 mg/kg/hour) immediately post CLP + Amipicillin (100 mg/kg i.p.) plus Gentamicin (4 mg/kg, i.p.) immediately post CLP + Injury |

Results

Figure 2:
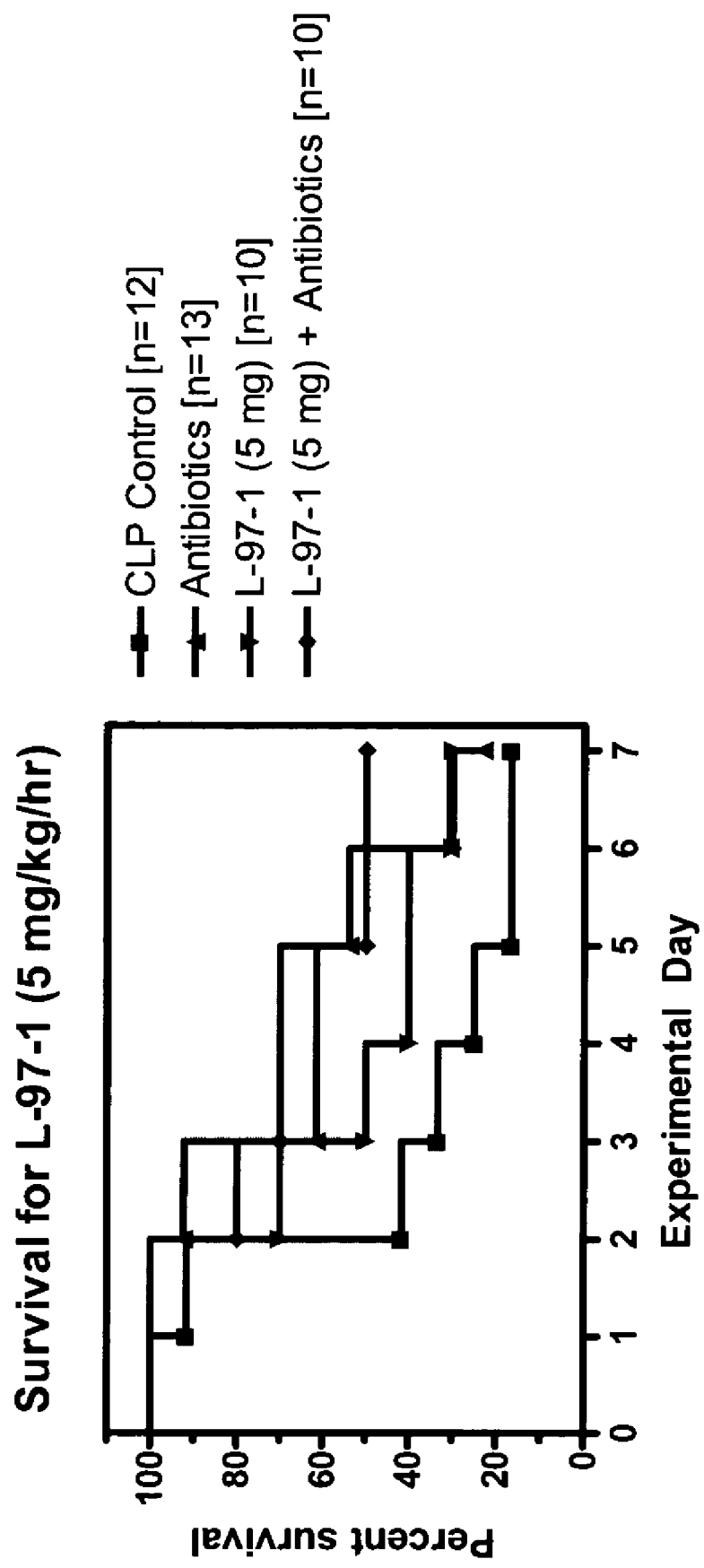
FIG. 2 provides the seven day survival rates for rats post-CLP treated with vehicle, antibiotics alone, L-97-1 alone (5 mg/kg/hr), or L-97-1 (5 mg/kg/hr) and antibiotics. Experimental details are provided in Example 3.
Figure 3:
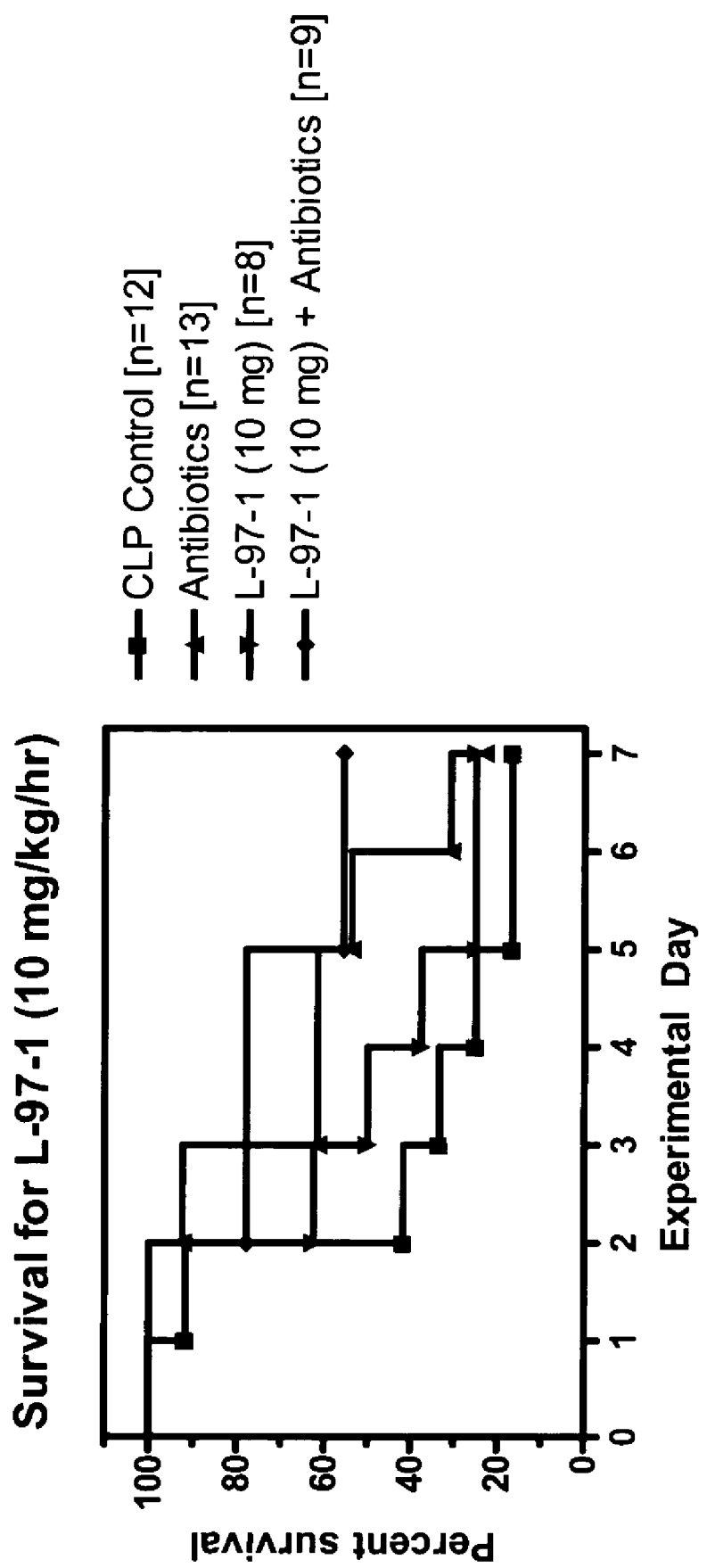
FIG. 3 provides the seven day survival rates for rats post-CLP treated with vehicle, antibiotics alone, L-97-1 alone (10 mg/kg/hr), or L-97-1 (10 mg/kg/hr) and antibiotics. Experimental details are provided in Example 3.
Figure 4:
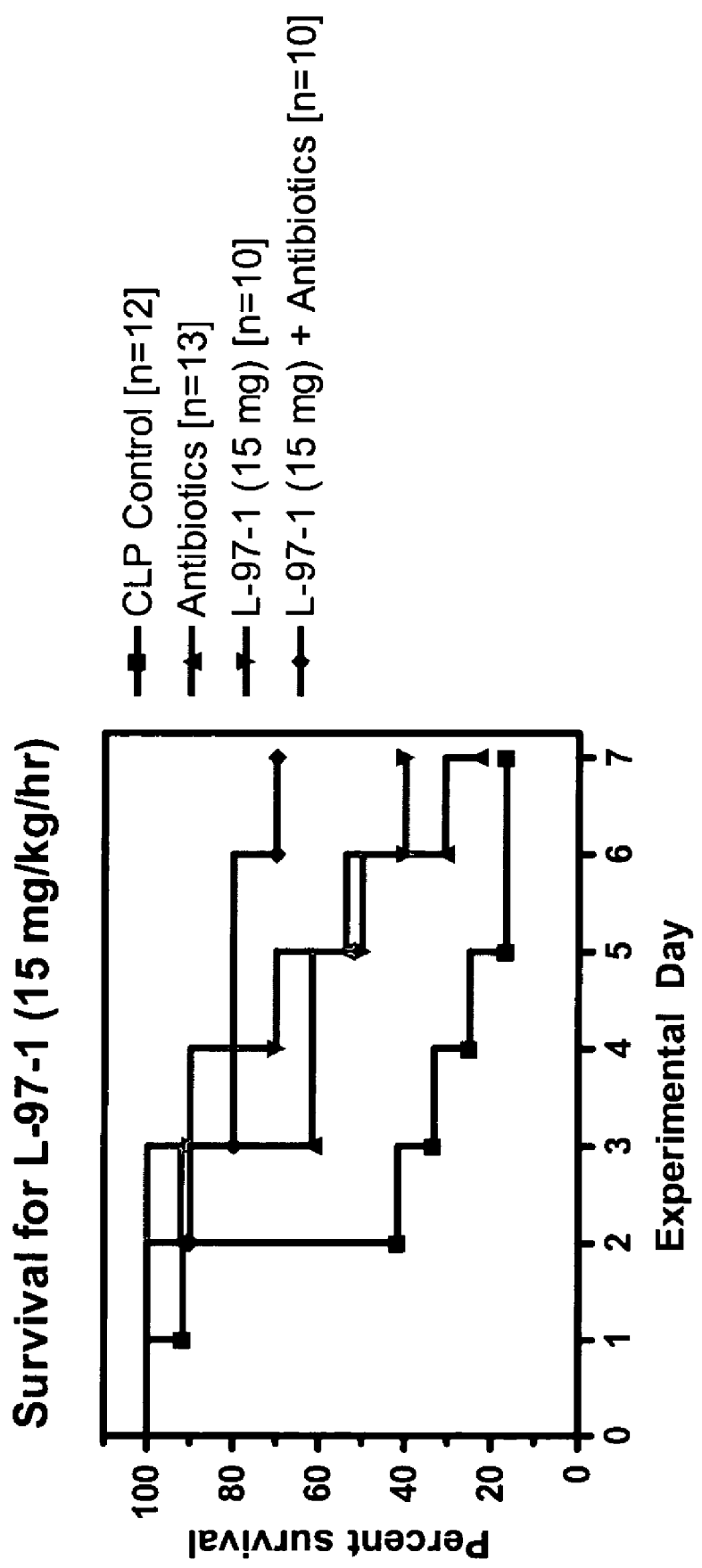
FIG. 4 provides the seven day survival rates for rats post-CLP treated with vehicle, antibiotics alone, L-97-1 alone (15 mg/kg/hr), or L-97-1 (15 mg/kg/hr) and antibiotics. Experimental details are provided in Example 3.

Seven day survival results are provided in FIGS. 1-4. Seven day survival rates for rats treated with L-97-1 and antibiotics were improved over those observed with either antibiotic or L-97-1 treatment alone.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of treating sepsis in a subject, the method comprising administering to the subject a therapeutically effective amount of an $A_1$ adenosine receptor antagonist in combination with an antibiotic agent used to treat sepsis, wherein the $A_1$ adenosine receptor antagonist is a compound of formula (I) in an amount sufficient to increase the survival rate of the subject wherein the compound of the formula (I) is:

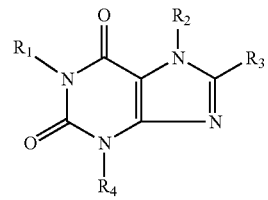

wherein $R_1$ is $C_3$ alkyl;
$R_2$ is:

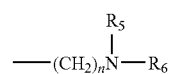

wherein n is 2; $R_5$ is $CH_3(CH_2)_p$, wherein p is 1; and $R_6$ is $(CH_2)_m OH$, wherein m is 2;
$R_3$ is:

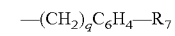

wherein q is 1; wherein $R_7$ is H; and $R_4$ is of the formula:

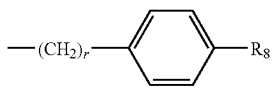

wherein $R_8$ is $NH_2$; and r is 2.

2. The method of claim 1, wherein the subject is a human patient.

3. The method of claim 1, wherein the antibiotic agent is a cephalosporin.

4. The method of claim 3, wherein the antibiotic agent is ceftazidime.

5. The method of claim 1, wherein the $A_1$ adenosine receptor antagonist and the antibiotic agent are administered sequentially.

6. The method of claim 1 wherein the $A_1$ adenosine receptor antagonist and the antibiotic agent are administered simultaneously.

7. The method of claim 1, wherein the $A_1$ adenosine receptor antagonist and the antibiotic agent are administered orally, intravenously or by pulmonary inhalation.

* * * * *